United States Patent [19]
Morais

[11] 4,036,057
[45] July 19, 1977

[54] AUTOMATIC THRESHOLD CONTROL MEANS AND THE USE THEREOF

[75] Inventor: Carroll F. Morais, Sacramento, Calif.

[73] Assignee: Acoustic Emission Technology Corporation, Sacramento, Calif.

[21] Appl. No.: 568,277

[22] Filed: Apr. 15, 1975

[51] Int. Cl.² ............................................. G01N 3/00
[52] U.S. Cl. .................................... 73/88 R; 73/71.4
[58] Field of Search ................. 73/88 R, 552, 557, 70, 73/35, 556, 555, 67.2, 71.4; 318/624; 340/172

[56] References Cited

U.S. PATENT DOCUMENTS

| | | | |
|---|---|---|---|
| 3,447,378 | 6/1969 | Dunegan et al. | 73/35 X |
| 3,456,493 | 7/1969 | Roddick | 73/35 |
| 3,733,424 | 5/1973 | Pitts et al. | 73/91 X |
| 3,822,586 | 8/1972 | Pollock | 73/88 AE UX |

Primary Examiner—Jerry W. Myracle
Attorney, Agent, or Firm—Mark C. Jacobs

[57] ABSTRACT

A threshold actuated information detection system comprising a noise level converter, and a non-inverting voltage totalizer, and a voltage comparator interconnected such that the comparator will not trigger any logic circuit if an amplified signal is lower than the threshold level, and the use thereof in acoustic emission and other informational discriminating systems.

15 Claims, 3 Drawing Figures

A. AUTOMATIC THRESHOLD METHOD -
DEADBAND REMAINS CONSTANT
• THRESHOLD TRIPPED

B. FIXED THRESHOLD METHOD -
THRESHOLD REMAINS CONSTANT
• NOISE OR SIGNAL TRIPPED WHEN EITHER IS ABOVE THRESHOLD LEVEL

COMPARISON OF AUTOMATIC & FIXED THRESHOLD METHODS
FOR
ACOUSTIC EMISSION SOURCE LOCATION & COUNTING

AUTOMATIC THRESHOLD CONTROL

AUTOMATIC THRESHOLD CONTROL MEANS AND THE USE THEREOF

BACKGROUND OF THE INVENTION

One of the problems associated with audio information detection systems is the problem of background noise and the determination of the threshold level. The problem of threshold level determination arises not only in detection systems, such as acoustic emission, but also in electronically controlled apparatuses and systems such as automatic car wash apparatuses that operate on the basis of audio sensing means to trigger each function, ie. scrub, dry, etc. Threshold level determination is often difficult due to the presence of ambient noise caused either by the apparatus itself or from the surroundings, such that one is not always sure of having the electrical function triggered by a truly intended signal. The problem of ambient noise is also associated with the difficulty of hearing a car radio when the vehicle is moving at high speed. The driver is forced to turn up the volume when driving at 55mph., to a level of volume which when the car is stopped as at a traffic light, seems almost deafening. This phenomenon is due to the fact that when the car is at rest, the ambient noise level is substantially lower than when the vehicle is moving. Thus in order to get response of the human ear to the audio signal, it is necessary to increase volume to overcome the level of the background noise. It could be said that the level at which the driver can hear the program material is the threshold or response level, at that particular speed and driving conditions for the vehicle.

Thus in U.S. Pat. No. 3,842,663 it was recognized that for a demodulated resonance analysis system, pertaining to the location of flaws in rotating and/or reciprocating machinery components, it was stated that the transducer(s) to be selected must be chosen with a concern toward the frequencies generated by parts of the machine system, as well as the nature of the background noise.

In the field of acoustic emission, the problem of threshold level can be significant. Extraneous low-frequency noise must be prevented from triggering the logic network. Often this is done by utilizing a threshold voltage level above the anticipated maximum background noise level to be incurred during the stressing, and this level is normally set prior to the start of the application of the stress technique to the article in question. Ofttimes however, this predetermination of voltage level is difficult to determine since a major portion of the noise increase is due to and is proportional to the increasing stress level. For example, in a cyclic stressing situation the background noise would increase as the stress level increases, and the noise would decrease as the stress level decreases. Therefore it is seen that one would be required to set threshold level values for the maximum stress level and/or the maximum noise level. However a threshold level set for the maximum noise situation could result in a loss of data during the lower noise or stress levels.

In view of the above, it is an object of the present invention to provide a threshold determination means which avoids the problems discussed above.

Another object of this invention is to provide an acoustic emission monitoring system which is responsive only to desired signals and not to ambient noise.

A further object is to provide a multi-channel acoustic emission monitoring system with an adjustable threshold level, the value thereof being constant in relation to the background noise level's upward and downward changes.

Yet another object is to provide an acoustic emission system whose data acceptance criteria are uninfluenced by sudden surges in background noise.

A still further object is to provide an acoustic emission monitoring system which is responsive only to desired signals and not to slow rising mechanical noise impulses.

One other object is to provide an improved threshold actuated information detection system.

Still another object is to provide a threshold actuated microseismic information determination system of improved capability.

One more object is to provide a more pleasingly operated car radio signal reception means.

SUMMARY OF THE INVENTION

In accordance with the above described objects, this invention pertains to an automatic threshold noise level control means. Preferably such means is incorporated into the post amplification stage when a two part amplification of the signal technique is employed. In operation the automatic threshold control (ATC) constitutes a circuit that monitors the background noise level continuously and generates a voltage that is equal to or slightly greater than the background noise level. This voltage level is added to the original threshold voltage level, as set by a threshold control neans — a technique known to the art — and the total voltage is bussed to one or more channels of the detection system as is desired. Such a control means allows the operator to set individual gain levels, and a threshold control to a predetermined deadband value. Deadband is defined as the difference between background noise level and the threshold level. It is seen that the deadband area will remain constant, whether the background level remains constant, or varies upward or downward. This assures the fact that each data channel of the system that is so interconnected is activated only by acoustic emission signals which exceed the preset deadband value.

Optionally, only the deadband is bussed to each operating channel, in those situations where each channel employs its own threshold; or a plurality of thresholds are employed for an equal or greater number of information channels. If desired, the background noise can be independently determined by the practitioner.

The above features and description of the invention will become evident by reference to the description of the preferred embodiment to follow.

*Only the analog section of the acoustic emission system is shown, since the nature of the logic system employed is not dependent upon the instant invention.

As is known in the art, acoustic emission monitoring systems comprise a technique for the measurement of stress waves. In operation, a series of sensors, usually piezoelectric crystals are applied to the pressure vessel or other structure for detection of the energy released as a result of plastic zone formation or incremental crack propagation within the structure being monitored. The energy release propagates through the structure as an elastic stress wave which is detected by the sensor which in turn provides an output signal in response to the stress wave's passage through the material. The output signal is amplified, processed and rendered available for use as by visual display or for operation of a computer upon the signal.

Figure 1:
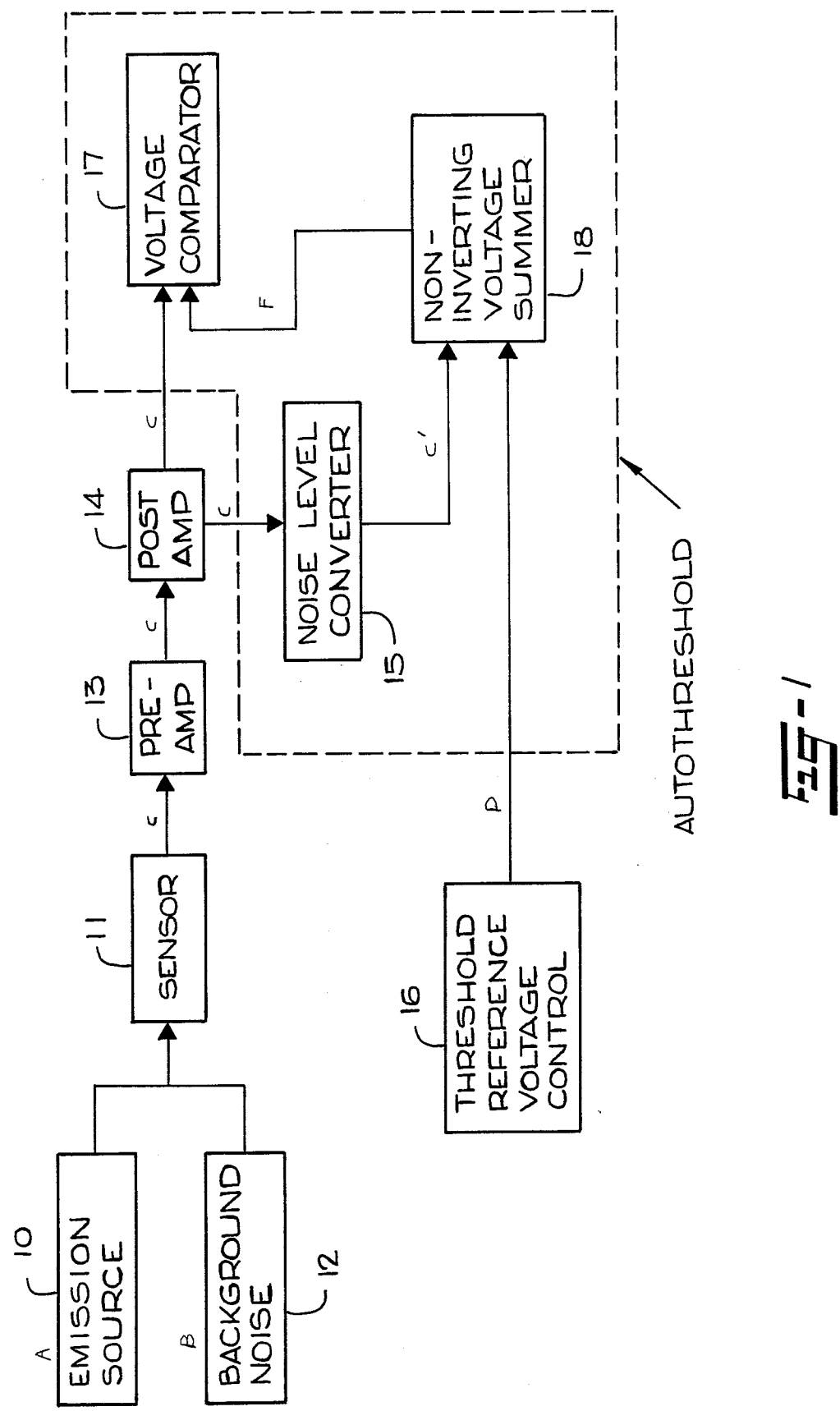
FIG. 1 is a block diagram of an acoustic emission monitoring system* that incorporates the present invention.

Referring now to FIG. 1, a block diagram of an acoustic emission monitoring system incorporating the present invention is shown. The sensor(s) 11 detect the energy release from the source of emission e.g. pressure vessel, 10, and the sensors also detect the background noise level 12. The output signal is fed to one or more amplification stages. Any filtration of the signal that may be desired is accomplished at this step. The signal from the post amplifier is fed to the noise level converter 15 where the voltage level of the incoming signal is converted. Here a DC voltage is generated in proportion to the detected voltage. This generated voltage is added to the threshold reference voltage which emanates from the threshold reference voltage control 16, by the, voltage totalizer 18, such circuitry for 16, 15 and 18 being known to the art for each separate component. Novelty lies in the new combination. This total voltage figure is fed to the comparator 17 which compares the raw signal from the post amp 14 with the signal from the totalizer 18. If the post amp signal is greater, then an output pulse is generated by the comparator and the apparatus functions. If the signal in the raw is lower or equal to that of the totalizer then no signal is issued. ( C < F, then no output signal ex comparator).

When a multichannel acoustic emission system is employed, the threshold level signal is bussed to all channels. With the use of a proper bussing arrangement, a plurality of threshold controls can be utilized with particular groups of channels. Such a group threshold control technique is most useful when one acoustic system is employed to monitor two or more independent test structures wherein each structure has a requirement of a different threshold value.

It is also to be seen within the scope of this invention to employ a multiplicity of threshold levels each being individually controllable and each hooked to a plurality of channels. Such a technique is readily employable in complex multi-channel acoustic emission systems, where the nature of or the level of background noise differs from monitoring zone to monitoring zone.

Figure 2:
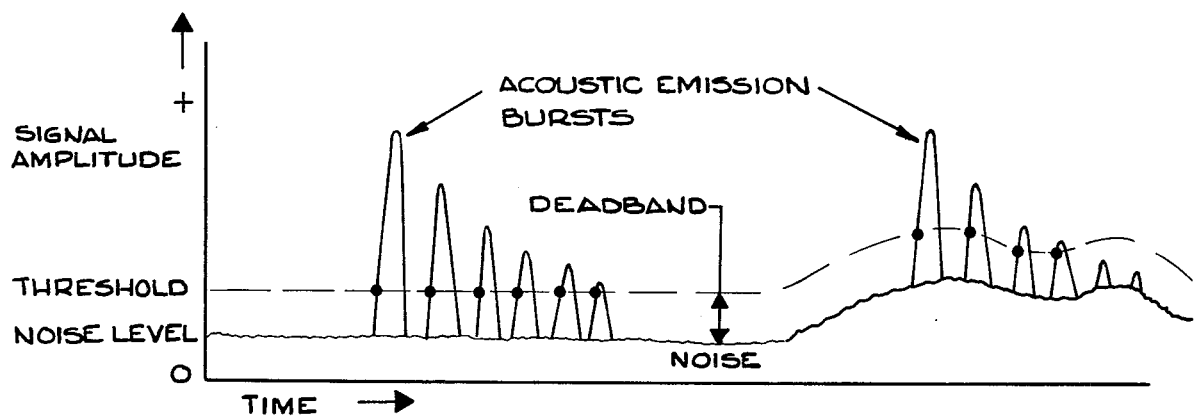
FIG. 2 is a comparison of an automatically variable threshold and a fixed threshold actuated acoustic emission source location and counting system.
Figure 2:
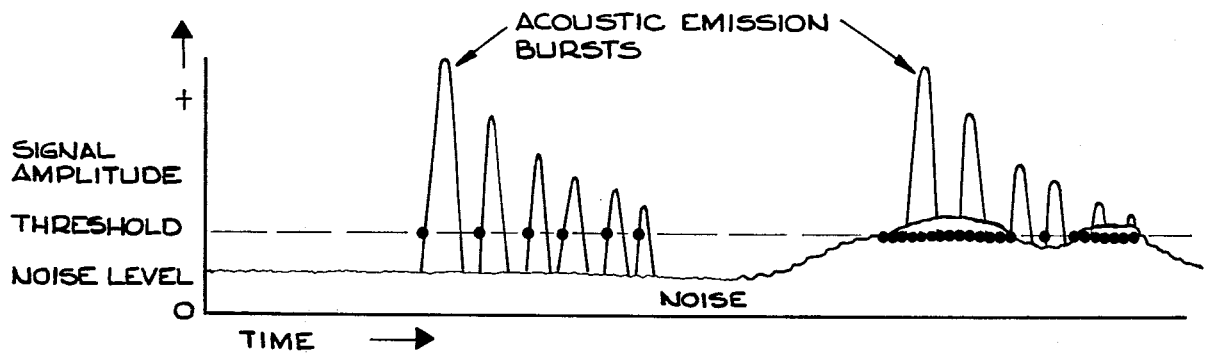

FIG. 2 diagramatically depicts a comparison of the automatic threshold (constantly variable) and a fixed threshold method for acoustic emission source location and counting. It is seen that in FIG. 2A, the "trips" take place at the threshold level which is always above the noise level, such that the acoustic emission bursts that are emitted, are true sources of information. While in the system of the prior art as shown in FIG. 2B, even though the trips all take place at the threshold level, such that the burst on the left side of the word NOISE in the figure all give rise to valid information, the trips on the right side of the figure give rise to true and false information. The bursts here arise both as a result of desired signals, and from the presence of ambient levels of noise that exceed the threshold level. For this reason a large multiplicity of trips are depicted in FIG. 2B, while the bursts represent only those arising as a result of true trips, ie. good information.

Figure 3:
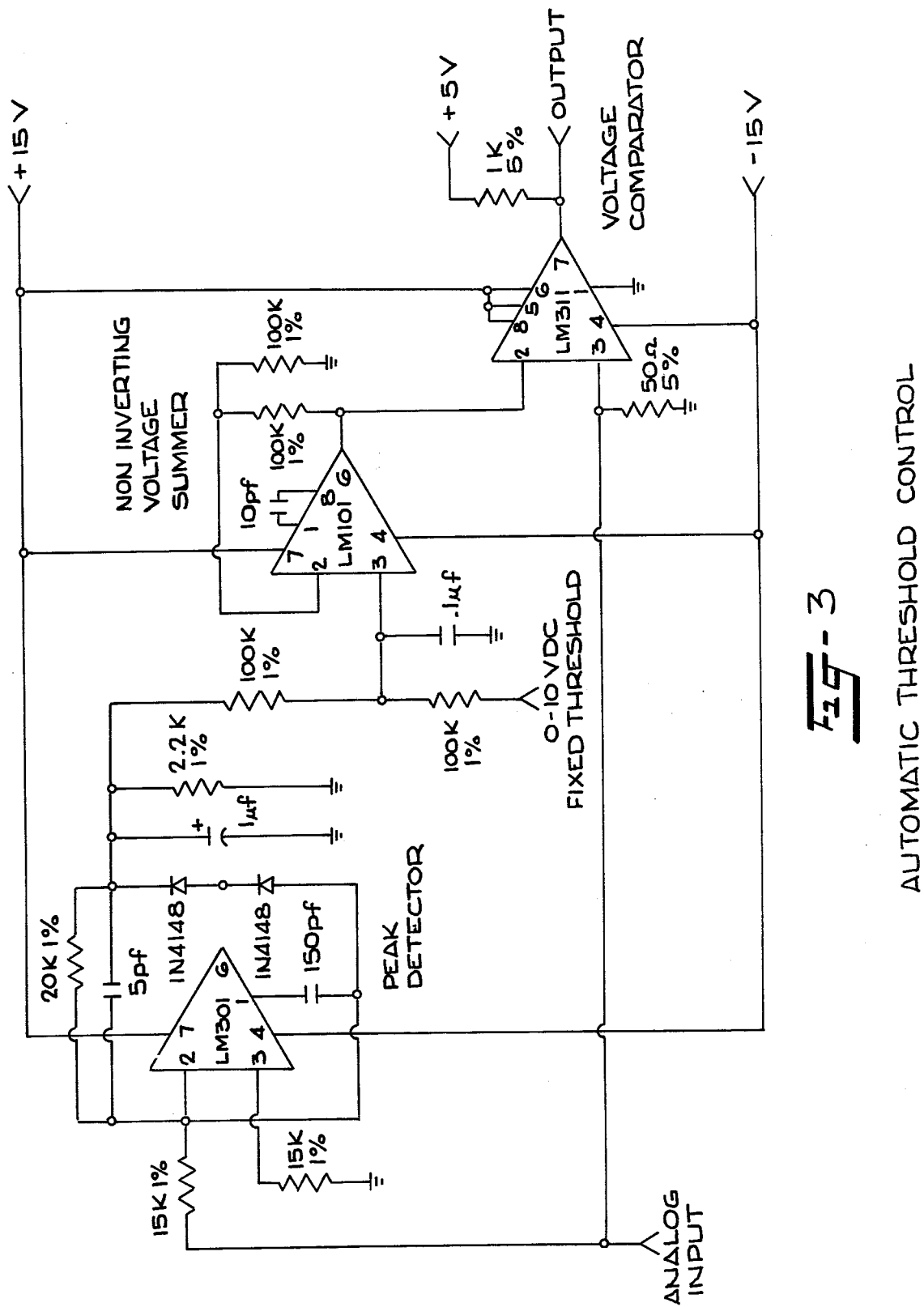
FIG. 3 is a schematic diagram of a circuit which will carry out the objects of the present invention, namely control the threshold level.

As can be seen in FIG. 1, the automatic threshold ie. continuously variable threshold level of this invention constitutes the apparatuses within the dotted line; namely the noise level converter 15, the voltage comparator 17, and the non-inverting voltage summer or totalizer 18. The schematic diagram of FIG. 3 depicts these three apparatuses tied together to accomplish the desired result herein. The circuits for the noise level converter, which is reality a peak detector circuit, the summer and for the comparator are easily understood by those skilled in the art. When each is considered singly and not as tied in combination in the unique manner of this invention, they are all found in the prior art. Stated in another way, the unique aspect here is the utilization of the peak detector to monitor the noise level of the input signal. This voltage is then taken and added to the normal threshold value that goes into the comparator such that the noise will not interfere with the system's operation.

Each of the three apparatuses comprises an operational amplifier with the LM + 3 digit number being the coding of a typical vendor of such items, namely National Semiconductor for the 3 different units employed herein. The peak detector's output signal is fed past two type IN4148 diodes, past a 100K ohm resistor to the totalizer, where it is joined by the signal from the threshold reference control voltage, entering the summer at pin 3. This total voltage is fed to the comparator which compares this voltage with the signal from the post amplification stage. If the voltage from the post amplification stage is greater, then an output pulse is generated from the comparator, as shown exiting from pin 7, such that an acoustic emission burst is emitted which is visible on a CRT if tied in a conventional manner. This burst would be a clean burst in that it represents the propagation of a flow or the growth of of a plastic zone, uninfluenced by ambient noise.

Many variations of the equipment and method described here exist to accomplish the desired result without departing from the spirit of the invention. Other types of devices may be used for each and all of the three components to carry out the same functions such as to lead to the overall desired effect. In addition it is seen that the invention is not limited to the use of two stage amplification acoustic emission monitoring systems. Thus the invention can be employed in the apparatus and method of Steele, Green and Lockman in U.S. Pat. No. 3,545,262 issued Dec. 8, 1970.

Furthermore, it is now readily seen that the automatic threshold control means of this invention is easily adapted for use in car radios. There, the background noise level would be speed dependent, and would also be influenced by the number of open windows and the noise from the engine and air conditioning system. As the noise level would increase, the delta or amount of change would influence the volume or output signal strength from the radio.

It is readily seen that the invention of this application, is quite important to sophisticated multi-channel acoustic emission systems. Most of such systems have a built in dead time, ie. a time period of a few or many milliseconds when all signals are locked out of the logic circuit. This deadtime commences when the last timing channel exceeds the threshold voltage thereby emitting a true or false burst. During this deadtime period no new data can be acquired, and one risks the loss of possible true data while the logic network is reset. In addition it is seen that clean bursts could mix with bursts arising as a result of high ambient noise levels thereby leading one to an inaccurate conclusion about the structure or structures being monitored, absent the use of the invention disclosed herein.

One advantage of the present invention is the fact that the threshold actuation means herein is employable over the entire frequency band, i.e. from DC through audio, through ultrasonic and to and through the RF band.

In the drawing of FIG. 1, and throughout the text herein only the analog portion of a detection system has been discussed. The comparator triggers a condition namely activation of the logic system of the nature employed, and not forming a part of this invention, and the logic manifests a response, be it the ringing of a bell, the raising of the volume of the radio, the stopping of a welding machine due to the existence of bad welds, or the operation of a time interval triangulation measurement locating device.

To further illustrate the broad applicability of the threshold actuated informational detection systems within the scope of this invention, mention should be made of microseismic systems which are used in mining rock structural analyses.

Microseismic detection systems detect the microseismic signals that emanate from microseismic events. By detecting the microseismic signals from each microseismic event that transpires within a mine by knowledge of the coordinates of each geophone (sensor) and the microseismic velocities, it is possible to calculate the origin coordinates for each event, and perhaps prevent disasters. These microseismic events arise due to stress changes in the rock structure and in general the rate of occurrence of these events in a given location is related to the structural stability of that location. Since drilling noise, movement of people, water perhaps, and railcars or other transportation devices, are involved, it is necessary to measure the events by analysis of a signal beyond a threshold level. Since the background noise can vary immensely under these operating conditions, the applicability of the instant invention is readily seen.

To recapitulate, especially with reference to the first Figure, it is seen that the automatic threshold control of this invention consists of three parts; namely (1) the continuous noise detector which tracks the peak value of the noise as received from the amplifier stage. The input signal is designated C in the Figure and constitutes a combination of stress waves, A, and background noise, designated B. The detector generates or converts the C signal to a new signal slightly larger than, or of equal proportion to the incoming signal C. This C' generated signal is of the peak value only and not peak to peak as for C. The (2) component is the non-inverting voltage summer which combines C' with D, which D is DC reference or fixed threshold value for component (3) the voltage comparator. The comparator has two signal inputs, one is C from the amplifier, and the other is F from the summer. The F signal inhibits the comparator from triggering the logic on continuous or slow rising system noise, but allows fast rising data to trigger the comparator. The comparator triggers counters, delta T logic or other time difference processor everytime the amplified acoustic emission or microseismic or other employed apparatus's emission signal crosses the DC threshold voltage by producing compatible pulses, usually of a digital nature.

Having fully described the invention, it is intended that it be limited only by the lawful scope of the appended claims.

What is claimed is:

1. An acoustic emission apparatus for the detection and/or location of structural flaws comprising sensor means, and means for receiving signals emitted from said sensor means and for determining the location of flaws in the workpiece being monitored, the improvement comprising an automatically variable threshold voltage level control means connected to said means for receiving signals from said sensor means.

2. An acoustic emission apparatus comprising a plurality of sensor means for detecting stress waves in the object being monitored, and means for continuously varying the threshold voltage level in proportion to the noise level as the noise level rises, falls or remains constant interconnected therewith.

3. An automatically variable threshold voltage level control means, comprising means for varying the threshold voltage level in proportion to the noise level as the noise level rises, falls or remains constant connected to a threshold reference voltage controller.

4. An improved threshold actuated information detection system comprising in combination: a peak detector noise level converter adapted to receive an amplified signal, a non-inverting voltage summer interconnected to said converter, and to a threshold reference voltage control, and a voltage comparator interconnected to said summer and adapted to receive the same amplified signal a the converter.

5. The threshold actuated information detection system of claim 4 further including a DC threshold reference voltage control connected to said summer.

6. The threshold actuated information detection system of claim 5 further including voltage amplification means interconnected to both said converter and said comparator.

7. The system of claim 6 further including sensing means interconnected to said voltage amplification means.

8. The threshold actuated information detection system of claim 4 further including voltage amplification means interconnected to both said converter and said comparator.

9. The system of claim 8 further including sensing means interconnected to voltage amplification means.

10. The method of automatically controlling the threshold voltage in a threshold actuated information detection system comprising:
   a. Generating a voltage equal to or greater than the background noise;
   b. Summing a predetermined threshold voltage level with the voltage of step (a);
   c. Comparing the summed voltage with a signal input voltage,
   d. controlling the actuation of a system responsive apparatus below the threshold voltage.

11. The method of claim 10 further including the step of triggering a system response apparatus when the signal input voltage is greater than summed voltage.

12. The method of claim 10 including the step of determining a constant threshold voltage level prior to the summing step.

13. The method of claim 12 including the step of measuring the background noise level prior to step(a).

14. The method of claim 12 including the step of sensing both the background noise and stress wave emissions, amplifying the sensed signals and feeding the amplified signals to both a noise level converter and to a voltage comparator, all prior to step (a).

15. In a microseismic detection system, comprising detection means, amplification means and a threshold level voltage generator, the improvement which comprises at least one automatically controlled threshold level actuating means for each channel of detection, and at least one channel of detection for each automatically controlled threshold level actuating means.

* * * * *